United States Patent [19]

Kwon

[11] Patent Number: 5,766,596
[45] Date of Patent: Jun. 16, 1998

[54] ACONITE TUBER-SULPHUR COMPOSITE PREPARATION AND A PROCESS FOR THE PREPARATION THEREOF

[75] Inventor: Jae Woo Kwon, Seoul, Rep. of Korea

[73] Assignee: Gollin Pharmaceutical Co., Ltd., Seoul, Rep. of Korea

[21] Appl. No.: 911,019

[22] Filed: Aug. 13, 1997

[30] Foreign Application Priority Data

Aug. 13, 1996 [KR] Rep. of Korea .................. 96-33496

[51] Int. Cl.$^6$ ..................... A61K 35/78; A61K 33/04
[52] U.S. Cl. ........................... 424/195.1; 424/714
[58] Field of Search ................... 424/195.1, 714

[56] References Cited

U.S. PATENT DOCUMENTS

| | | | |
|---|---|---|---|
| 4,352,796 | 10/1982 | Arichi et al. | 424/195 |
| 5,198,230 | 3/1993 | Wen | 424/525 |
| 5,290,784 | 3/1994 | Qu et al. | 514/279 |
| 5,547,956 | 8/1996 | Qu et al. | 514/279 |

*Primary Examiner*—Raymond Henley, III
*Attorney, Agent, or Firm*—Birch, Stewart, Kolasch & Birch, LLP

[57] ABSTRACT

An oriental aconite tuber-sulphur composite preparation which is used for treating the withdrawal syndromes of various narcotic patients and alcoholics is disclosed. The aconite tuber-sulphur composite medicine comprises in weight %: 75–80% of pharmaceutically acceptable sulphur precipitatum, 5–7% of chemically treated mica, 0.8–1.2% of alum, 0.7–0.9% of a non-toxic aconite tuber, 1–13% of an adhesive and a proper amount of water, whereby above ingredients are agitated to make a paste, and tablets of 4 mg each are prepared. Owing to these ingredients, the central nervous system of narcotic addicts and alcoholics are tranquilized so as to cure the abstinence symptoms. Thus their pains are alleviated, and the abstinence symptoms are cured in a short period of time. Further, the administration of the medicine of the present invention does not cause any secondary addictions, and there is no apprehension that the symptoms may return. Unlike the treatment with chlorpromazine, there is no adverse reaction, and therefore, the medicine of the present invention gives beneficial effects to narcotic addicts and alcoholics.

12 Claims, 1 Drawing Sheet

ACONITE TUBER-SULPHUR COMPOSITE PREPARATION AND A PROCESS FOR THE PREPARATION THEREOF

BACKGROUND OF THE INVENTION

1. Field of the Invention

The present invention relates to an oriental aconite tuber-sulphur composite preparation which is used for treating the withdrawal syndromes of various narcotics patients and alcoholics.

2. Description of the Related Art

The toxicosis from using various narcotics such as morphine, heroin, philophone, cocaine and the like cause social problems all over the world.

The toxicosis patients have personal and social problems. If these problems are to be eliminated, first legal measures and mental treatment and drug treatment have to be carried out.

Viewed from medical science, the drug addicted patients encounter difficulties in giving up narcotics, because they feel pain upon withdrawing from the narcotics.

Therefore, in the conventional methods for treating the withdrawal syndrome, patients are resorted to: a tapering method in which the use of the narcotics is gradually reduced; a substitution method in which the drug is substituted with methadone (which is also a narcotic); and a tranquilizing method in which chlorpromazine (which is an anti-psychotic drug) is administered. Furthermore, a continuous sleeping method, a shock method and a steroid administration method are used.

Among the above mentioned treating methods, the methadone substituting method is not desirable because methadone itself is toxic. The chlorpromazine method somewhat alleviates the syndrome, but its efficacy is not very high, and there are adverse effects such as extra pyramidal symptoms and the like. Other adverse effects of the chlorpromazine treatment include sickly feeling, nausea and insomnia. Furthermore, the treatment period is lengthy, and the symptoms return after the termination of the treatment.

SUMMARY OF THE INVENTION

The present invention is intended to overcome the above described disadvantages of the conventional techniques.

Therefore it is an object of the present invention to provide an orally administered aconite tuber-sulphur composite oriental medicine composed of aconite-tuber, sulphur precipitatum, mica and alum, which is effective for treating without adverse effect the symptoms caused by abstaining from drugs such as morphine, heroin, philophone, cocaine and the like, and the habitual alcoholics, and in which recurrence of the symptom does not appear.

The present invention, unlike conventional drugs, contains a small amount of aconite tuber in which the toxicity of the aconitic alkaloid has been substantially removed by thermally processing the aconite tuber. The present invention further includes chemically treated mica, sulphur precipitatum, and alum which is a silicate. These ingredients are formed into a paste by using starch. Then tablets are formed from the paste, so that oral ingestion would be easy. Use of this medicine results in very short periods of symptoms from abstinence and the recurrence of the symptoms do not appear after the completion of the treatment.

BRIEF DESCRIPTION OF THE DRAWINGS

The above object and other advantages of the present invention will become more apparent by describing in detail the preferred embodiment of the present invention with reference to the attached drawings in which.

DETAILED DESCRIPTION OF THE PREFERRED EMBODIMENT

Figure 1:
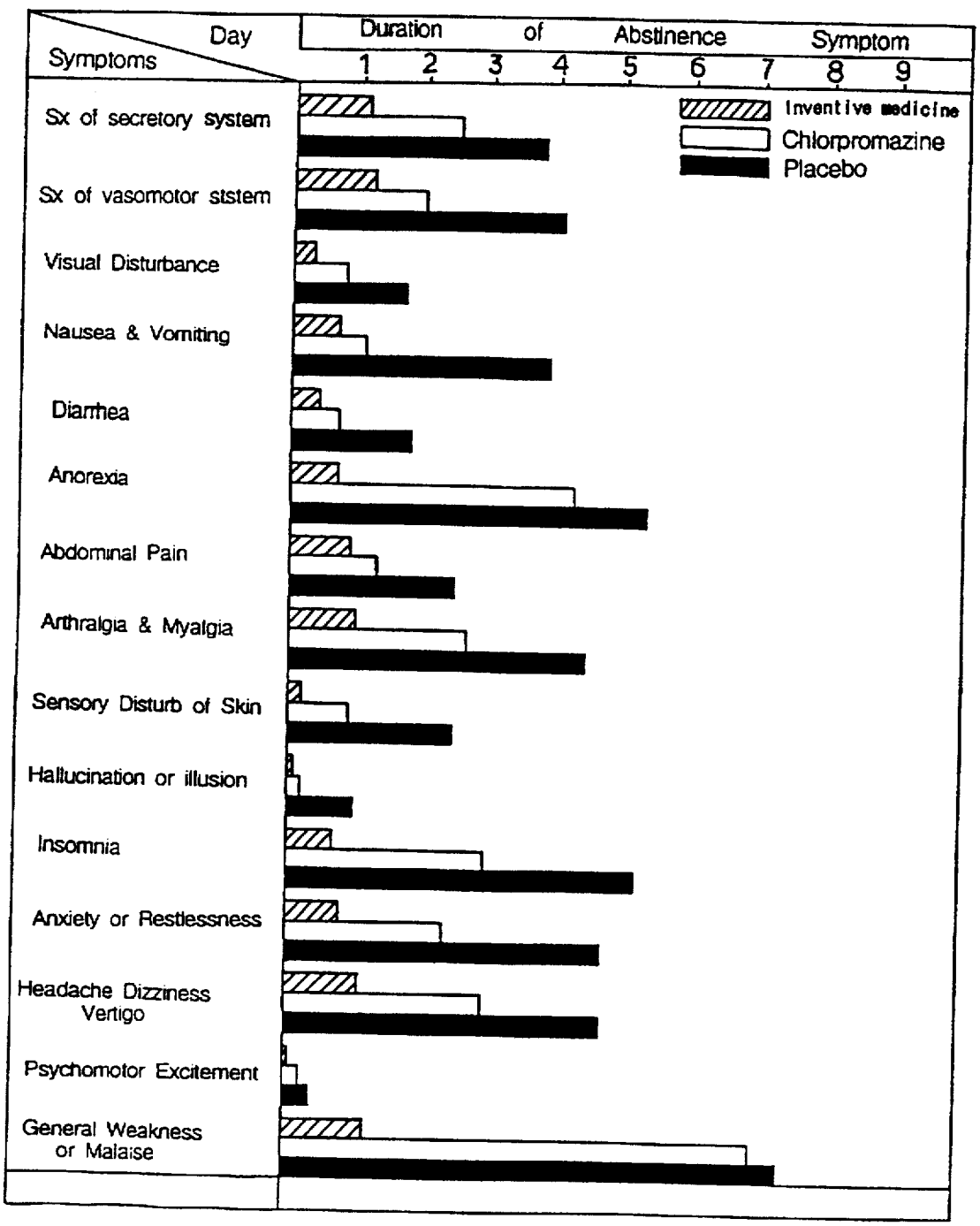
FIG. 1 is a graphical illustration showing the abstinence symptom treating period for drug addicts when the medicine of the present invention is used.

The medicine according to the present invention is composed of in weight %: about 75–80% of sulphur precipitatum, about 5–7% of mica, about 0.8–1.2% of alum, and about 0.7–0.9% of aconite tuber. Further, about 10–13% of an adhesive such as starch and a small amount of water are added to make the mixture into a paste. Then the paste is formed into tablets, so that oral administration would be easy.

The amount of ingredients in the aconite tuber-sulphur composite medicine according to the present invention per tablet are about 4 mg of aconite tuber, about 20 mg of mica, about 400 mg of sulphur, and about 5 mg of alum.

The ingredients are chemically stable with each other, and the amount of the ingredients are decided by considering the medical requirements. That is, the content of the ingredients are the basic amounts for an adult, and the dosage may be adjusted (increased or decreased) depending on the severity of the symptom.

The sulphur which is used in the present invention is sulphur precipitatum (crystalline sulphur) which is in a pharmaceutically acceptable form. Sulphur is classified into non-crystalline sulphur and crystalline sulphur, and the former is toxic to the human body, while the latter is not toxic to the human body. Sometimes, crystalline sulphur contains a small amount of non-crystalline sulphur, and therefore, the crystalline sulphur is purified before using it.

The purification of the crystalline sulphur is carried out in the following manner. The crystalline sulphur is heated to 120° C. to melt it, and the impurities are made to be suspended. Then the impurities are removed, and thus the crystalline sulphur is purified. Then the melted sulphur is put into cold water to solidify it. Crystalline sulphur is dissolved in carbon disulfide ($CS_2$), but non-crystalline sulphur is not dissolved in it. By utilizing this property, the dried crystalline sulphur is put into carbon disulfide to dissolve it. Then the non-dissolved non-crystalline sulphur is removed by filtering it. Then carbon disulfide is recovered by vaporizing it.

As described in the Oriental Medicinal Scripture (Dongeibogam), mica is put into a smokeless furnace, and is heated until it becomes red. Then it is cooled and water-washed. Then it is dried, and crushed into powder.

Alum, which is a silicate, should be purified into a pharmaceutically acceptable form. That is, alum is put into a ceramic crucible, and it is heated for about 4 hours, until it is melted to a white stuff. Then it is taken out, and cooled. Then it is crushed into a white powder. In the oriental medicine, it is called "goban".

Preferably, aconite tuber is used in a processed form. Aconite tuber is put into an extraction pot, and ethyl alcohol having a concentration of 60% is injected until aconite tuber is submerged. Then the lid of the pot is closed, and heated for about 40 minutes at a temperature of 100°–120° C. Thus the aconitine alkaloid which is contained in aconite tuber is extracted, thereby obtaining a non-toxic aconite tuber. Then it is dried and crushed into a powder.

Aconite tuber is very toxic, and therefore, if too much is ingested, a fatal result may result. The major ingredient of aconite tuber is alkaloid aconite, and there are further included ingredients such as mesaconite, pyraconitine, hypaconitine, benzaconitine and the like. Even at present, analysis for the ingredients is being carried out.

In the present invention, there is used a processed aconite tuber, and this processed aconite tuber is non-toxic. That is, the alkaloid which is the toxic ingredient of the aconite tuber is bonded with alkamine (having two organic acid frames) in the form of an ester. Particularly, an ester bonded with acetic acid forms a mono-ester by heat or by alkaline compound. This non-ester type alkaloid has a toxicity of ¹/₁₅₀–¹/₂₀₀ compared with the original alkaloid. Further, if one ester portion is cut away to become alkamine, then the toxicity is lowered to ¹/₂₀₀₀.

Among the various ingredients, the toxicity of mesaconitine (which is heat-decomposed), particularly the toxicity of pyromesaconitine is very weak.

The aconite tuber of the present invention has lost the toxic component through heat treatment, and thus it is processed into an ingredient having almost no toxicity.

Further, the ingredients of the composite aconite tuber-sulphur medicine are individually oriental medicines.

Unlike conventional medicine, the ingredients of the aconite tuber-sulphur composite medicine acts singly or individually to cure the abstinence symptoms of narcotic addicts.

Sulphur is basically used as a sterilizer in Western medicine. It is used in the oriental medicine as a sterilizer for psoriasis. It is also used for warming cold feet, and for reinforcing muscular bones (Oriental Medicine Scripture).

When the aconite tuber-sulphur composite medicine is ingested, the sulphur component which is introduced into the human body is converted into a sulfide, and about 30% of the ingested amount is absorbed. Sulphur in the blood is discharged through the kidney in the form of sulfites and sulfates, while a part of it is discharged through the lungs in the form of H2S gas. In this process, it is known that sulphur lowers the concentration of alcohol in the blood. That is, in a living body, various compounds become non-toxic by being conjugated with the sulfates.

The source of the sulfate which is widely used for the conjugation includes methionine and cysteine which are sulphur-containing amino acids. The sulphur component participates in the metabolism of alcohol, and this fact should not be overlooked. Experimentally, it is known that the sulphur component lowers the concentration of alcohol, but which one of ADH pathway or MEOS pathway is more affected is a subject of further study.

Mica is a non-toxic mineral, and in the oriental medicine, it is administered to reinforce the gastro-intestinal tract.

Alum tastes sour and puckery, and is used as an anti-inflammatory agent for treating ozena and teeth.

In the present invention, mica and alum are effective for giving power to bodily powerlessness.

Aconite tuber is the root of Ranunculaceae, and due to its strong toxicity, it is normally not used in Western medicine. However, it is used in the Oriental medicine in small amounts together with other toxicides as medicine by boiling it.

In the international pharmaceutical society, it is provided that the oral dose of aconitine should be 100 µg at a time, and at most, 200 µg at a time and 500 µg per day. Therefore, the processed powder of aconite tuber may be safely administered in the amount of 0.5–1.0 g per day. Rather, even if aconite-tuber according to the present invention is administered in larger amounts in accordance with the severity of the symptoms, there will be no fatal effect.

The various ingredients of the treated aconite tuber, particularly alkaloid aconitine have a sedative effect by acting on the brain Further, they also act on the peripheral nerves, and make the perceptive nerve dull.

These ingredients cooperate with the non-alkaloid components, and in this view, they are different from the non-alkaloids. That is, the non-alkaloid component which is contained in the treated aconite tuber has a significantly lowered toxicity to the cardiac function, and it also acts as an analgesic. Thus the pain during the abstinence period is alleviated, and therefore, the drug addiction can be overcome. Particularly, aconitine shows no special toxicity, and therefore, it is very suitable for treating the habitual drug addiction.

In the present invention, clinical experiments were carried out in the following manner.

EXAMPLES

1. Experiment on the abstinence symptom of morphine addicted mouse.

(1) Experimental preparation and reagent

The aconite tuber-sulphur composite preparation according to the present invention was formed into a powder. Then it was suspended in a 0.9% physiological salt solution to form 10 g/100 ml. Morphine (morphine HCl) was diluted in the physiological salt solution of Jeil Pharmaceutical Company, and naxalon was diluted in the physiological salt solution of Samjin Pharmaceutical Company.

(2) Experimental animal

One hundred and twenty ICR family male mice having a bodily weight of 20–25 g were made ready. They were fed for 7 days with commercial solid feeding stuff, and the amount of the feeding stuff and water was not restricted. The animals were classified into: a morphine 20 mg/Kg (of body weight) administered group (Group I); a morphine 400 mg/Kg (of body weight) administered group (Group II); a group in which only the aconite tuber-sulphur according to the present invention is administered (Group III); and a physiological salt solution administered group (Group IV). Group I was separated into: a group in which only morphine was administered (first addicted group); and a group in which 20 mg/Kg of morphine and 200 mg/Kg of the aconite tuber sulphur composite preparation were administered (first treating group). Group II was divided into two groups, one of which was administered with 40 mg/kg (of body weight) and the other administered with the composite preparation of the present invention (Treatment Group II). The mice were allocated in a number of 20 to each group.

(3) Morphine addiction inducement and administration of medicine

For the first addicted group (Group I), morphine was parenterally injected in an amount of 20 mg/Kg of body weight once every day for 14 days.

For the first treating group (Group I), first morphine injections were carried out for 7 days, and then, the aconite tuber-sulphur composite medicine of the present invention was orally administered in an amount of 200 mg/Kg of body weight.

For the second addicted group (Group II), morphine was parenterally administered in an amount of 40 mg/Kg of body weight at every 8 hours for 6 days (18 times).

For the second treating group (Group II), the aconite tuber-sulphur composite medicine was orally administered in an amount of 200 mg/Kg of body weight, and then, morphine was parenterally injected 3 times every day.

For all the animals, the body weight was measured before the experiments, and the variation of the body weight was observed during the experiments.

(4) Results and evaluations (Regarding the body weight)

The body weight of the addicted group (Group I) increased by 1.4% during the experimental period after the administration of 20 mg/Kg (of body weight) of morphine, while the body weight of the treated group was decreased by 1.9%.

The body weight of the morphine 40 mg/Kg (of body weight) administered group (Group II) decreased by 7.5%. The group which was also given the treatment (Treatment Group II) showed a body weight decrease by 8.0%. The body weight of a comparative group (Group IV) was increased by 15.4%. The group which was administered only with the composite preparation of the present invention (Group III) showed an increase of body weight by 15.0%.

From the above results, the following fact could be known. That is, the greater the administered amount of morphine, the variation of the body weight was so much greater. However, the administration of the aconite tuber-sulphur composite medicine of the present invention had no relation to the variation of the body weight.

(Result of treatment)

For the mice of the first addicted group in which 20 mg/Kg (of body weight) of morphine had been administered, after 8 hours from the last morphine administration, naloxone was administered peritoneally in an amount of 4 mg/Kg (of body weight). Then they were put into a slightly dark cylindrical compartment having a radius of 35 cm and a height of 70 cm for 30 minutes.

Then the leaping response, the appearance of the abstinence symptoms and the effect of the medicine of the present invention were observed.

The leaping average was 30.2±15.4 times.

The group in which the medicine of the present invention was administered showed a leaping average of 6.4±4.6.

This shows that the aconite tuber-sulphur composite medicine of the present invention significantly decreased the symptom of the morphine addiction.

In the morphine 40 mg/Kg addicted group, the leaping average was 156.3±60.8.

In the treated group in which the medicine of the present invention was administered, the leaping average was 11.7±10.8. This shows that the symptom of the addiction of morphine has been significantly decreased.

In the group in which only the medicine of the present invention was administered, and in the comparative group in which a physiological salt solution was administered, there was no leaping response.

2. Clinical experiments on narcotics addicts (1) Experimental preparation and method From among the patients who were hospitalized in the psychiatric department of the Seoul National University Hospital, 68 male addicts and 10 female addicts were selected. In this selection, those having no abstinence symptom, those having other bodily disorders, those showing severe nausea and those refusing experiments were excluded.

The age of the selected patients was 23–67, and the average age was 39.50±10.03. They had used 0.2–4.0 mg of heroin through parenteral administration every day, and the period of the use was 1–30 years.

At the same time, they had used other drugs such as seconal, phenobarbital, codeine, pyrine, baralgin and cod eggs.

Their past hospitalization was 0–23 times.

They were divided into 3 groups in accordance with the above data.

The group in which the medicine of the present invention was administered included 35 persons. The group in which chlorpromazine was administered consisted of 23 persons. The group in which a placebo was administered consisted of 20 persons. The administration method and the dosage were as shown in Table 1 below.

TABLE 1

| | | The Method of Medication | | |
|---|---|---|---|---|
| | Number of | | Duration of Medication | |
| Group | Individuals | Dosage | Mean (day) | Range (day) |
| Present Invention | 38 | 28 gm–63 gm (40–90T)/day.p.o | 8.03 | 7–9 |
| Chlor-promazine | 23 | 400–1.500 mg/day, p.o | 8.5 | 7–9 |
| Placebo | 20 | same as this invention | 8.62 | 7–9 |

The administration of the medicines were started in 2 hours from the appearance of the abstinence symptom. For only the first 1–3 days, 40–90 tablets (containing 0.7 mg of aconite tuber per tablet) were administered. Then in accordance with the disappearance of the abstinence symptom, the dosage was reduced to ⅓–¼. In the case of chlorpromazine, its amount was reduced in accordance with the alleviation of the abstinence symptom.

The abstinence symptom dissipation period in accordance with the administration of the medicines and the critical ratios of the 3 groups are shown in Table 2 below. FIG. 1 is a graphical illustration for Table 2.

TABLE 2

The Duration of Abstinence Symptom in the Treatment with
the Present Invention Contrasted with Chlorpromazine &
Placebo, Evaluated with Critical Ratio (determined with
Number of Days)

| | Placebo | | Chlorpromazine N = 23 | | | Present Invention (N = 35) | | | |
|---|---|---|---|---|---|---|---|---|---|
| | N = 20 | | | | CR to | | | CR to | CR to |
| Symptom | Mean | S.D. | Mean | S.D. | Plac. | Mean | S.D. | Plac. | CZ |
| Sx of secretory system | 3.80 | 2.96 | 2.45 | 1.83 | 2.37 | 1.09 | 1.57 | 3.02 | 6.19 |
| Sx of vasomotor system | 4.15 | 2.71 | 2.00 | 2.33 | 4.88 | 1.17 | 1.53 | 3.50 | 2.08 |
| Visual disturbance | 1.55 | 2.29 | 0.87 | 1.59 | 1.83 | 0.23 | 0.59 | 2.55 | 1.83 |
| Mausea & vomiting | 3.95 | 2.16 | 1.17 | 1.77 | 5.72 | 0.63 | 1.03 | 7.06 | 3.18 |
| Diarrhea | 1.75 | 2.20 | 0.05 | 1.55 | 3.00 | 0.32 | 0.69 | 2.86 | 3.30 |
| Anorexia | 5.40 | 2.75 | 4.30 | 2.79 | 1.46 | 0.69 | 1.47 | 10.47 | 10.81 |
| Abiominal pain | 2.40 | 2.87 | 1.30 | 1.14 | 2.11 | 0.83 | 1.30 | 2.31 | 2.24 |
| Arthralg a, myalgia | 5.00 | 3.16 | 2.61 | 2.48 | 3.14 | 0.94 | 1.73 | 7.00 | 4.64 |
| Sensory disturb skin | 2.35 | 2.90 | 0.91 | 1.44 | 2.82 | 0.20 | 0.40 | 3.32 | 7.55 |
| Hallucination, illusion | 0.95 | 2.10 | 0.15 | 0.83 | 3.20 | 0.03 | 0.33 | 3.56 | 1.50 |
| Insomnia | 5.40 | 3.32 | 3.00 | 2.47 | 2.11 | 0.60 | 1.17 | 8.03 | 7.55 |
| Anxiety, restlessness | 4.80 | 2.59 | 2.43 | 1.05 | 3.11 | 0.94 | 1.22 | 10.16 | 8.28 |
| Headache, dizziness, etc | 4.80 | 2.95 | 2.87 | 2.54 | 2.81 | 1.09 | 1.18 | 8.06 | 6.36 |
| Psychomotor excitement | 0.40 | 0.92 | 0.30 | 0.86 | 0.13 | 0.03 | 0.17 | 0.89 | 0.84 |
| General weakness | 7.35 | 1.26 | 0.96 | 1.57 | 2.16 | 1.71 | 1.97 | 29.37 | 27.31 |
| Confusion | 2 cases | | case | | | no case | | | |
| Generalized convulsion | 1 case | | 1 case | | | no case | | | |
| Incteased appetite | 1 case | | no case | | | 28 caes | | | |

In Table 2 above, the values were obtained in the following manner. That is, starting from 12 hours after the administration of medicine, the appearance of the abstinence symptom was observed at every 12 hours, and then the appearances of the abstinence symptoms were averaged. The critical ratio shows the difference between the 3 groups.

The overall results as the consequence of the administration of the medicines are shown in Table 3 below.

TABLE 3

Result of the Treatment with this invention, Chlorpromagazine and Placebo, evaluated with the Intensity of Symptom (% of individuals)

| Result | Present Invention | Chlor-promazine | Placebo |
|---|---|---|---|
| Excellent | 23 (65.71%) | 5 (21.74%) | 2 (10.00%) |
| Fair | 10 (28.57%) | 13 (56.52%) | 4 (20.00%) |
| Poor | 2 (5.72%) | 5 (21.74%) | 14 (70.00%) |
| Total | 35 (100%) | 23 (100%) | 20 (100%) |

In Table 2 above, the experiment and observation periods were 8 days, and therefore, some symptoms may continue for more than 8 days. However, as shown in FIG. 1, the group in which the medicine of the present invention was administered did not show any symptom is beyond 48 hours, although some abstinence symptoms were sustained in the chlorpromazine group and in the placebo group. This means that the efficacy of the medicine of the present invention is excellent compared with the efficacy of the conventional medicines.

In Table 3 above, "Excellent" refers to those who did not show any or only very meager amounts of abstinence symptoms. "Fair" refers to those who had some abstinence symptoms, but who could relatively easily bear the pain. "Poor" refers to those who had severe abstinence symptoms and severely suffered from the pain.

The excellent results were 10.00% in the placebo group, and 21.74% in the chlorpromazine group, while the present invention medicine group showed an excellent result of 65.71% Poor results were seen by 70.00% in the placebo group and by 21.74% in the chlorpromazine group, while the present invention medicine group showed poor results by only 5.72%.

This witnesses to the fact that the aconite tuber-sulphur composite medicine gives a wonderful effect to the drug abstinence symptoms.

The variations in the body weight of the patients during the treatment of the abstinence symptoms were as shown in Table 4 below.

TABLE 4

| Group | No. of Individuals | Mean Body Weight Change | S.D. | P | Individuals With Increased Body Wt. |
|---|---|---|---|---|---|
| Present Invention | 35 | −2.06 (Kg) | ±3.22 | — | 8 |
| Chlorpromazine | 28 | −5.07 (Kg) | ±2.83 | .01 | 0 |
| Placebo | 20 | −9.30 (Kg) | ±2.14 | .01 | 0 |

During the treatment period, almost all the patients showed decreased body weights, but in the case of the present invention medicine group, 8 cases showed body weight increases.

Medical research on the medicine of the present invention should be carried out more specifically in the future, but it has been already proved that the medicine of the present invention gives an excellent effect to curing the narcotic abstinence symptoms.

3. Liquor spirit experiment on rabbits (1) Experimental preparation and method

The experimental animals were mature rabbits having a body weight of about 2 Kg. They were used without discriminating between male and female. The animal" were divided into: a comparative group in which only a liquor spirit is administered; and a group in which the medicine of the present invention and a liquor spirit were administered.

Five tablets of the aconite tuber-sulphur composite medicine according to the present invention were dissolved in 15 cc of distilled water, and this was orally administered through a catheter 20 minutes before the administration of the liquor spirit. One tablet of the medicine of the present invention which was used contained 4 mg of aconite tuber, 400 mg of sulphur, 20 mg of mica and a small amount of alum.

The liquor spirit was ethanol having a concentration of 50 volume %, and 50.0 ml/Kg (of the body weight) was slowly parenterally administered for 5 minutes, so that a drunken behavior can be produced.

From 15 to 30 minutes after the administration of the liquor spirit, a cardiocentesis was carried out, and EDTA was used as the blood clatter. The concentration of the liquor the blood was measured by applying the Levin & Bodansky method.

(2) Experimental results

The variation of the concentration within the blood during the administration of the liquor spirit and the medicine of the present invention was as shown in Table 5 below.

TABLE 5

| Blood Taking Time | No. of Rabbits | Only Liquor Spirit (mean ± S.E. mg/ml) | No. of Rabbits | Liquor Spirit + gollin (mean ± S.E. mg/ml) | P |
|---|---|---|---|---|---|
| 10 min. | 10 | 2.07 ± 0.01 | 10 | 1.40 ± 0.05 | P < .05 |
| 30 min. | 10 | 1.41 ± 0.02 | 10 | 1.00 ± 0.02 | P < .05 |

In Table 5 above, the group in which the medicine of the present invention was administered before the administration of the liquor spirit showed a markedly low intra-blood concentration. Particularly, the difference was significant at 10 minutes rather than at 30 minutes.

(3) Observation

Alcohol metabolism is done mainly in liver, and about 20% of the metabolism is done in kidney and muscles.

The first step of the alcohol metabolism is oxidation for being converted into acetaldehyde. In this reaction, the enzyme, alcohol dehydrogenase (ADH) and catalase microsomal ethanol oxidin system (MEOS) participate.

It is a fact that the administration of the medicine of the present invention lowers the intra-blood spirit concentration. Which of the pathways of ADH and MEOS has given greater influence can be known through further experiments. However, the metabolism of sulphur is more well known than that of aconite. Further, since mica and alum are contained in the medicine of the present invention in addition to aconite and sulphur, other various therapeutic actions are expected.

As a result of the experiment, it was known that primarily the metabolism of alcohol is promoted, and secondarily the central nervous system is tranquilized. Therefore, the medicine of the present invention is effective for alcoholics.

According to the present invention as described above, the medicine includes sulphur precipitatum, mica, alum and a small amount of processed aconite which is very low in the toxicity. Owing to these ingredients, the central nervous system of narcotic addicts and alcoholics are tranquilized so as to cure the abstinence symptoms. Thus their pain is alleviated, and the abstinence symptoms are cured in a short period of time. Further, the administration of the medicine of the present invention does not cause any secondary addictions, and there is no apprehension that the symptoms may return. Unlike the treatment with chlorpromazine, there is no adverse reaction, and therefore, the medicine of the present invention gives beneficent effects to narcotic addicts and alcoholics.

What is claimed is:

1. An aconite tuber-sulphur composite medicine comprising in weight %: about 75–85% of pharmaceutically acceptable sulphur precipitatum and about 0.7–0.9% of aconite tuber.

2. The aconite tuber-sulphur composite medicine according to claim 1 which further comprises mica, alum and an adhesive.

3. The aconite tuber-sulphur composite medicine according to claim 2, wherein the weight % of said mica, alum and adhesive are about 5–7% of mica, about 0.8–1.2% of alum and about 10–13% of an adhesive.

4. The aconite tuber-sulphur composite medicine according to claim 1, wherein said aconite tuber is processed aconite tuber, wherein said processed aconite tuber is made by heating aconite tuber at 100–120 degrees C. in a solution of 60% ethyl alcohol whereby toxic aconitine alkaloid component is extracted out.

5. The aconite tuber-sulphur composite medicine according to claim 1, wherein the pharmaceutically acceptable sulphur is made by:

heating sulphur at 120 degrees C. in order to remove impurities, cooling melted sulphur with cold water, drying the sulphur, and dissolving the sulphur in carbon disulfide ($CS_2$).

6. A tablet comprising the aconite tuber-sulphur composite medicine according to claim 1.

7. A tablet comprising the aconite tuber-sulphur composite medicine according to claim 2.

8. A tablet comprising the aconite tuber-sulphur composite medicine according to claim 3.

9. A tablet according to claim 1, wherein one tablet contains about 4 mg or aconite tuber, 20 mg of mica, 400 mg of pharmaceutically acceptable sulphur precipitatum, 5 mg of alum and 60 mg of an adhesive.

10. A method of treating withdrawal syndromes of narcotics addicted patients and alcoholics, comprising administering to the patient an effective amount of the aconite tuber-sulphur composite medicine according to claim 1.

11. A method of treating withdrawal syndromes of narcotics addicted patients or alcoholics comprising administering to the patient an effective amount of the tablet according to claim 6.

12. The method according to claim 10, wherein said narcotics include morphine, heroin, philophone and cocaine.

* * * * *